United States Patent [19]

Ikeda et al.

[11] Patent Number: 5,062,307

[45] Date of Patent: Nov. 5, 1991

[54] STRAIN DETECTOR

[75] Inventors: Hideo Ikeda; Chiyo Hamamura; Hiroshi Satoh; Yoshihiko Utsui, all of Hyogo, Japan

[73] Assignee: Mitsubishi Denki Kabushiki Kaisha, Tokyo, Japan

[21] Appl. No.: 514,801

[22] Filed: Apr. 26, 1990

[30] Foreign Application Priority Data

| Apr. 27, 1989 | [JP] | Japan | 1-109713 |
| Apr. 27, 1989 | [JP] | Japan | 1-109715 |
| May 17, 1989 | [JP] | Japan | 1-123311 |
| May 17, 1989 | [JP] | Japan | 1-123312 |

[51] Int. Cl.$^5$ ............................................. G01L 3/10
[52] U.S. Cl. ................................................. 73/862.36
[58] Field of Search ..................................... 73/862.36

[56] References Cited

U.S. PATENT DOCUMENTS 3,861,206 1/1975 Kawafune et al. .
4,414,855 11/1983 Iwasaki .

FOREIGN PATENT DOCUMENTS 0260821 12/1985 Japan ................................. 73/862.36
0294322 12/1986 Japan ................................. 73/862.36
0223536 9/1988 Japan ................................. 73/862.36

OTHER PUBLICATIONS

IEEE Transactions on Magnetics, I. Sasada et al, vol. MAG-20, No. 5, Sep. 1984.

Primary Examiner—Charles A. Ruehl
Attorney, Agent, or Firm—Sughrue, Mion, Zinn, Macpeak and Seas

[57] ABSTRACT

A strain detector wherein external and internal magnetic fields are magnetically separated from each other to eliminate an influence of such disturbance magnetic field to assure accurate and stabilized detection of strain in a drive shaft. The detector comprises a magnetic layer made of a soft magnetic material having a high permeability and suitable magnetostriction fixedly mounted on an outer periphery of a driven shaft, a pair of bearings or bearing stands made of a soft magnetic material having a high permeability for supporting the driven shaft for rotation thereon, a detecting coil disposed around the magnetic layer for detecting a variation of the permeability of the magnetic layer arising from strain of the magnetic layer caused by an external force applied to the driven shaft, and a shield disposed on an outer periphery of the detecting coil and magnetically connected at the axial opposite end portions thereof to the bearings or bearing stands.

4 Claims, 5 Drawing Sheets

STRAIN DETECTOR

BACKGROUND OF THE INVENTION

1. Field of the Invention

This invention relates to a strain detector for detecting strain in a driven shaft such as, for example, a rotary shaft when an external torque or force is applied to the shaft.

2. Description of the Prior Art

Various strain detectors for detecting strain in a driven shaft are conventionally provided. An exemplary one of such detectors is disclosed, for example, in Japanese Kopai No. 57-211030, as shown in FIG. 8. Referring to FIG. 8, a driven shaft 40 in the form of a rotary shaft which is an object for the detection of strain is made of a non-magnetic material and supported for rotation around a center axis 46 by means of a pair of bearings 41 and 42. The bearings 41 and 42 are made of a non-magnetic material and supported on support members 43 and 44, respectively, which are also made of a non-magnetic material. A magnetic layer 45 made of a soft magnetic material having a high permeability is fixedly mounted on an outer periphery of the driven shaft 40. The magnetic layer 45 is composed of a plurality of parallel layer stripes which extend at an angle of −45 degrees with respect to the center axis 46. A cylindrical coil bobbin 47 made of a non-magnetic insulating material is disposed around the driven shaft 40 and supported on the support members 43 and 44. A detecting coil 48 is wound on the bobbin 47 and includes a pair of coil sections 48a and 48b.

With the strain detector of the construction described above, if an external torque or force is applied to the driven shaft 40, then strain is produced on the magnetic layer 45 to change the permeability of the driven shaft 40. The detecting coil 48 detects a variation of the permeability of the magnetic layer 45 as a variation in magnetic impedance, and a detecting circuit 14 (FIG. 9) detects and develops a strain detection output.

If a disturbance magnetic field from the outside acts upon the strain detector described above, such disturbance magnetic field tends to penetrate into the inside of the detecting coil 48. Here, since the drive shaft 40, bearings 41 and 42 and support members 43 and 44 are all made of non-magnetic materials, magnetic fluxes of the penetrating disturbance magnetic field pass through the magnetic layer 45 made of a magnetic material. Consequently, the magnetic operating point of the magnetic layer is displaced, which will cause an error in the output of the strain detector. Therefore, it is helpful to differentially amplify outputs of the coil sections 48a and 48b of the detecting coil 48 to cancel an influence of the disturbance magnetic field. However, since the magnetic characteristic is not symmetrical an error arising from a disturbance magnetic field is not removed completely, and accordingly, a sufficiently high degree of accuracy cannot be attained and stabilized detection of strain cannot be attained.

Another conventional strain detector is shown in FIG. 9. Referring to FIG. 9, a driven shaft 1 in the form of a rotary shaft is supported for rotation around a center axis 2 by means of a pair of bearings 3 and 4. A pair of elongated magnetic layers 5 and 6 made of a soft magnetic material having a high permeability and suitable magnetostriction are fixedly mounted on an outer periphery of the driven shaft 1 in a spaced relationship from each other in an axial direction of the driven shaft 1. Each of the magnetic layers 5 and 6 is composed of a plurality of parallel layer stripes which extend at angles of +45 degrees and −45 degrees with respect to the center axis 2, respectively. A cylindrical coil bobbin 7 is supported on the bearings 3 and 4 and disposed around the magnetic layers 5 and 6 in a concentric relationship to the driven shaft 1. A pair of detecting coils 8 and 9 are wound on the coil bobbin 7 corresponding to the magnetic layers 5 and 6, respectively. The detecting coils 8 and 9 are connected to a detecting circuit 14. A pair of yokes 10 and 11 made of a PC Permalloy containing about 80 percent by weight of nickel are disposed around the detecting coils 8 and 9, respectively. A first non-magnetic shield 12 made of a non-magnetic material having a high electric conductivity such as copper or aluminum is disposed commonly on outer peripheries of the yokes 10 and 11. A second magnetic shield 13 made of a soft magnetic material having a high permeability such as PC Permalloy is disposed around the first shield 12.

With this construction, if an external torque or force is applied to the driven shaft 1, then a tensile force is produced on either one of the magnetic layers 5 and 6 while a compression force is produced on the other of the magnetic layers 5 and 6, thereby causing the magnetic layers 5 and 6 to be strained. The magnetostriction of the magnetic layers 5 and 6 allows the orientation of the magnetization within each domain to be altered by such strain, which varies the permeability of the magnetic layers 5 and 6. In this instance, the permeability is varied in the opposite direction whether the strain is caused by a tensile force or a compression force. Each of the detecting coils 8 and 9 detects a variation of the permeability of the detecting coil 8 or 9 as a variation in magnetic impedance, and the detecting circuit 14 receives outputs of the detecting coils 8 and 9 and develops a detection voltage V corresponding to an amount of strain of the driven shaft 1. The yokes 10 and 11 converge magnetic fluxes produced by the detecting coils 8 and 9 to prevent leakage of magnetic fluxes from the detector to improve its sensitivity. Since the first shield 12 is formed from a non-magnetic material having a high electric conductivity, the depth of penetration of alternating magnetic fluxes is reduced to a very small value. Consequently, internal magnetic fluxes and external magnetic fluxes are magnetically separated from each other by the first shield 12. Accordingly, leakage of internal magnetic fluxes is prevented to raise the sensitivity of the detector while invasion of an external magnetic field into the detector is prevented to improve its noise preventing property. Further, since the second shield 13 is formed from a PC permalloy, it prevents invasion mainly of external direct current magnetic fluxes into the detector.

With this strain detector, however, since the first shield 12 has a simple cylindrical configuration, it cannot sufficiently prevent axial invasion of an external alternating current magnetic field and axial leakage of an internal magnetic field into and from the detector. Consequently, external magnetic fluxes, particularly direct current magnetic fluxes, flow though the magnetic layers 5 and 6 so that the operating point of each of them is displaced to cause an error in the detection of strain by the detector, and to deteriorate the sensitivity of the distortion detector. Further, where the detecting coils 8 and 9 are disposed close to each other, a magnetic interference takes place between them, which causes an error in detection of distortion. Accordingly, miniaturization of the distortion detector is difficult.

SUMMARY OF THE INVENTION

It is an object of the present invention to provide a strain detector wherein an influence of a disturbance magnetic field is eliminated to assure accurate and stabilized detection of strain in a drive shaft.

It is another object of the present invention to provide a strain detector wherein an external magnetic field and an internal magnetic field or a pair of detecting coils are magnetically separated from each other to improve the detecting sensitivity and the noise preventing property and attain miniaturization of the detector.

It is a further object of the present invention to provide a strain detector wherein axial invasion of an external direct current magnetic field is prevented effectively to improve the detecting sensitivity and assure accurate detection.

In order to attain the object, according the present invention, there is provided a detector for detecting strain in a driven shaft to which an external force is applied, which comprises a magnetic layer made of a soft magnetic material having a high permeability and suitable magnetostriction fixedly mounted on an outer periphery of the driven shaft, a pair of bearings or bearing stands made of a soft magnetic material having a high permeability for supporting the driven shaft for rotation thereon, a detecting coil disposed around the magnetic layer for detecting a variation of the permeability of the magnetic layer arising from strain of the magnetic layer caused by an external force applied to the driven shaft, and a shield disposed on an outer periphery of the detecting coil and magnetically connected at its axially opposite end portions to the bearings or bearing stands.

With this detector, since the bearings or bearing stands are made of a soft magnetic material having a high permeability and the shield is magnetically connected at the axially opposite end portions thereof to the bearings or bearing stands, an internal magnetic field and an external magnetic field are separated from each other by the shield, and consequently, invasion of an external magnetic field and leakage of an internal magnetic field into and from the detector is prevented with certainty.

The shield may be made of a soft magnetic material having a high permeability or a non-magnetic material having a high electric conductivity, and has a pair of flanges formed radially inwardly from the opposite ends thereof in such a manner as to have a channel-shaped section taken in a plane defined by the axial line and a radial line of the shield. Where the shield has such a channel-shaped section, an internal magnetic field and an external magnetic field are separated from each other not only in a diametrical direction but also in an axial direction of the driven shaft by the shield. Consequently, invasion of an external magnetic field and leakage of an internal magnetic field into and from the strain detector can be prevented with certainty.

The above and other objects, features and advantages of the present invention will become apparent from the following description and the appended claims, taken in conjunction with the accompanying drawings in which like parts are denoted by like reference characters all through the drawings.

DESCRIPTION OF THE PREFERRED EMBODIMENTS

Figure 1:
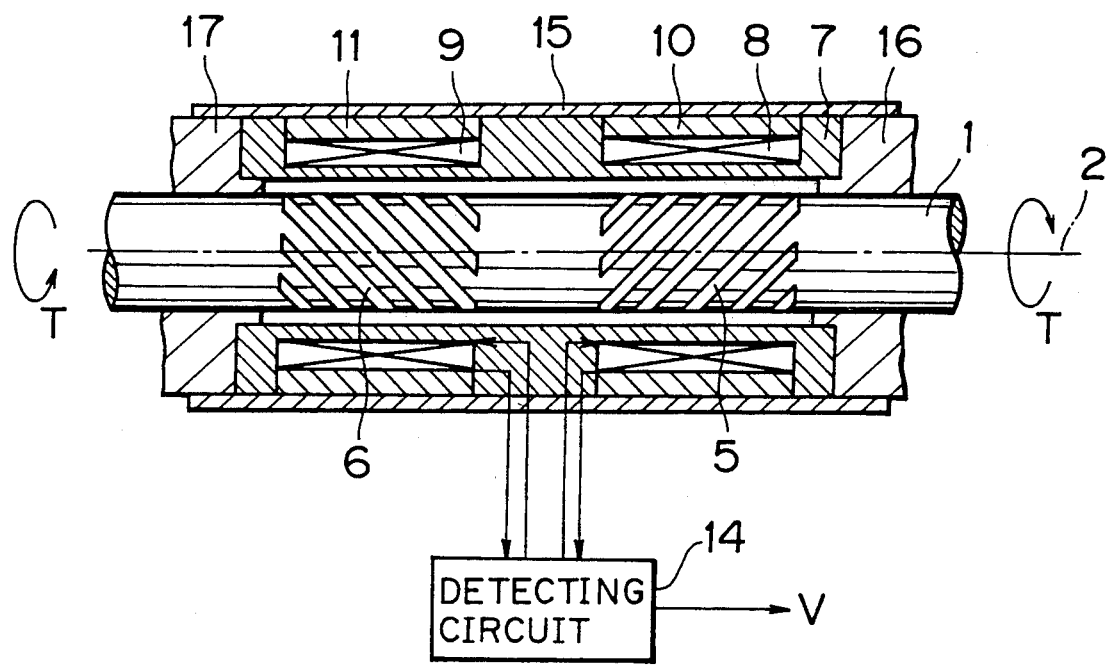
FIG. 1 is a schematic sectional view of a strain detector showing a first preferred embodiment of the present invention.

Referring first to FIG. 1, there is shown a strain detector according to a first preferred embodiment of the present invention. The detector shown is provided to detect strain in a driven shaft 1 in the form of a rotary shaft supported for rotation around a center axis 2 by means of a pair of bearing stands 16 and 17 formed from a soft magnetic material having a high permeability such as a PC Permalloy or pure iron. The detector includes first and second magnetic layers 5 and 6 made of a soft magnetic material having a high permeability and suitable magnetostriction fixedly mounted on an outer periphery of the driven shaft 1 in a spaced relationship from each other in an axial direction of the driven shaft 1. Each of the magnetic layers 5 and 6 is composed of a plurality of parallel layer stripes, and the stripes of the first magnetic layer 5 extend at an angle of +45 degrees with respect to the center axis 2 while the stripes of the second magnetic layer 6 extend at another angle of −45 degrees with respect to the center axis 2. A cylindrical coil bobbin 7 is supported on the bearing stands 16 and 17 and disposed around the magnetic layers 5 and 6 in a concentric relationship around the driven shaft 1. A pair of detecting coils 8 and 9 are wound on the coil bobbin 7 corresponding to the magnetic layers 5 and 6, respectively. The detecting coils 8 and 9 are connected to a detecting circuit 14. A pair of magnetic converging layers 10 and 11 made of a soft magnetic material having a high permeability are disposed around the detecting coils 8 and 9, respectively. A shield 15 made of a soft magnetic material having a high permeability such as a PC Permalloy or pure iron is disposed on outer peripheries of the magnetic converging layers 10 and 11 and magnetically connected at the opposite ends thereof to the bearing stands 16 and 17.

With this detector, if an external torque or force is applied to the driven shaft 1, then a tensile force is produced on either one of the magnetic layers 5 and 6 while a compression force is produced on the other of the magnetic layers 5 and 6, thereby causing strain of the magnetic layers 5 and 6. The magnetostriction of the magnetic layers 5 and 6 allows the orientation of the magnetization within each domain to be altered by such strain, which varies the permeability of the magnetic layers 5 and 6. In this instance, the permeability is varied in the opposite direction whether the strain is caused by a tensile force or a compression force. Each of the detecting coils 8 and 9 detects a variation in the permeability of the magnetic layer 5 or 6 as a variation in magnetic impedance, and the detecting circuit 14 differentially amplifies outputs of the detecting coils 8 and 9 and develops a detection voltage V corresponding to an amount of strain in the driven shaft 1. Since the magnetic converging layers 10 and 11 have a high permeability, they reduce the magnetic reluctance to magnetic fluxes produced by the detecting coils 8 and 9 and consequently raise the sensitivity of the detector. Also the shield 15 acts in a similar manner.

Here, in case an external magnetic field acts axially in parallel to the center axis 2 of the driven shaft 1, for example, from a location outside the bearing stand 16, since the bearing stands 16 and 17 and the shield 15 are high in permeability, magnetic fluxes of the external magnetic field pass first through the bearing stand 16 and then through the shield 15 and the other bearing stand 17 but do not pass through the magnetic layers 5 and 6. On the other hand, in case an external magnetic field acts diametrically in a direction perpendicular to the center axis 2, magnetic fluxes of the external magnetic field pass first through the shield 15 and then separately through the bearing stands 16 and 17 and finally through the shield 15 again but do not pass through the magnetic layers 5 and 6. Accordingly, the magnetic operating points of the magnetic layers 5 and 6 will not be displaced by an external magnetic field, and consequently, no error will take place in the output of the detector.

Further, with the detector of the embodiment described above, the shield 15 is supported at the opposite ends thereof on the bearing stands 16 and 17, and accordingly, the supporting mechanism therefor has a simplified construction. It is to be noted that it is only necessary for the shield 15 and the bearing stands 16 and 17 to be magnetically coupled to each other, and an air gap or some other member may otherwise be interposed between the shield 15 and each of the bearing stands 16 and 17.

Figure 2:
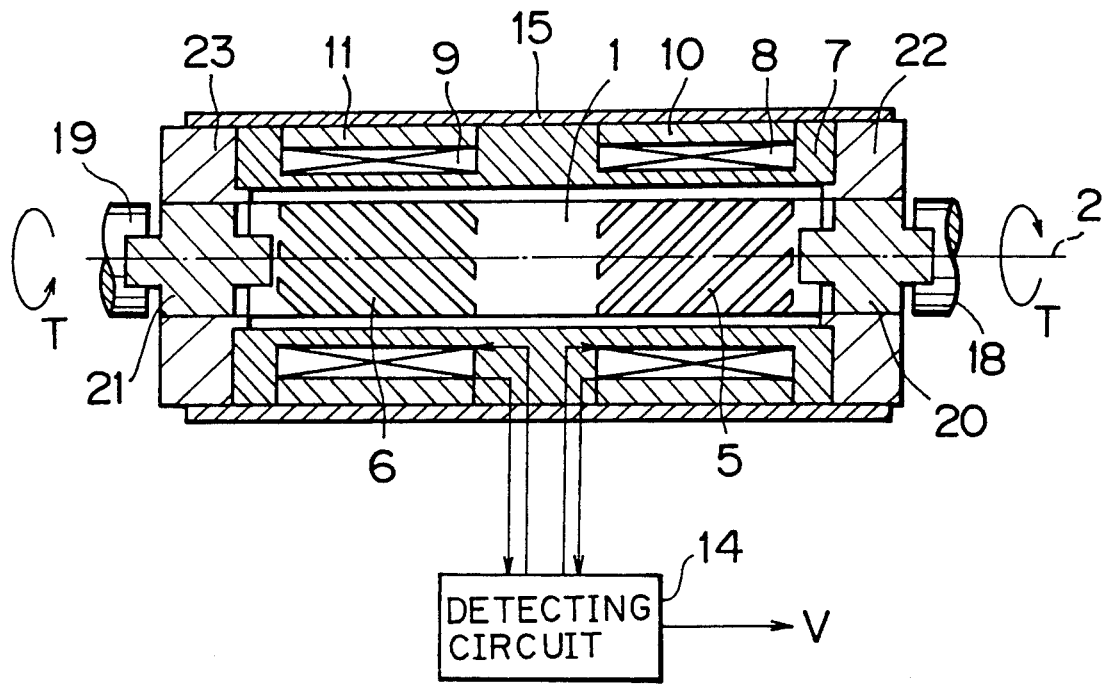
FIG. 2 is a similar view but showing a second preferred embodiment of the present invention.

Referring now to FIG. 2, there is shown a strain detector of a second preferred embodiment of the present invention. The detector of this embodiment has a generally similar construction to that of the first embodiment described hereinabove, but differs in that the driven shaft 1 is removably connected at the opposite ends thereof to a pair of rotary shafts 18 and 19 by way of connecting members 20 and 21 which are supported for rotation on bearings 22 and 23, respectively. The connecting members 20 and 21 and bearings 22 and 23 are each formed from a soft magnetic material having a high permeability such as a PC permalloy or pure iron. The bearings 22 and 23 are magnetically connected to the opposite ends of the shield 15.

If an external torque or force is applied to the driven shaft 1 from the rotary shafts 22 and 23 by way of the connecting members 20 and 21, then the driven shaft 1 is deformed and the detecting circuit 14 develops a detection voltage V corresponding to an amount of strain in the driven shaft 1 in a similar manner as in the detector of the preceding embodiment.

Meanwhile, if an external magnetic field acts axially parallel to the center axis 2 of the driven shaft 1, for example, from a location outside the bearing 22, since the connecting members 20 and 21, bearings 22 and 23 and shield 15 are high in permeability, magnetic fluxes of the external magnetic field pass from the connecting member 20 through the bearing 22, shield 15 and the other bearing 23 and connecting member 21 but do not pass through the magnetic layers 5 and 6. On the other hand, in case an external magnetic field acts diametrically in a direction perpendicular to the center axis 2, magnetic fluxes of the external magnetic field pass first through the shield 15 and then separately through the bearings 22 and 23 and connecting members 20 and 21 and finally through the shield 15 again to the outside but do not pass through the magnetic layers 5 and 6. Accordingly, the magnetic operating points of the magnetic layers 5 and 6 will not be displaced by an external magnetic field, and consequently, no error will take place in the output of the detector.

It is to be noted that, while the shield 15 in the detector of the present embodiment is supported at the opposite ends thereof on the bearings 22 and 23, it is only necessary for the shield 15 and the bearings 22 and 23 to be magnetically coupled to each other and they need not necessarily be connected directly to each other. Further, while the driven shaft 1 may be made of a magnetic material, it is preferably made of a non-magnetic material because it is effective to eliminate a possible influence of a disturbance magnetic field upon the magnetic layers 5 and 6.

Figure 3:
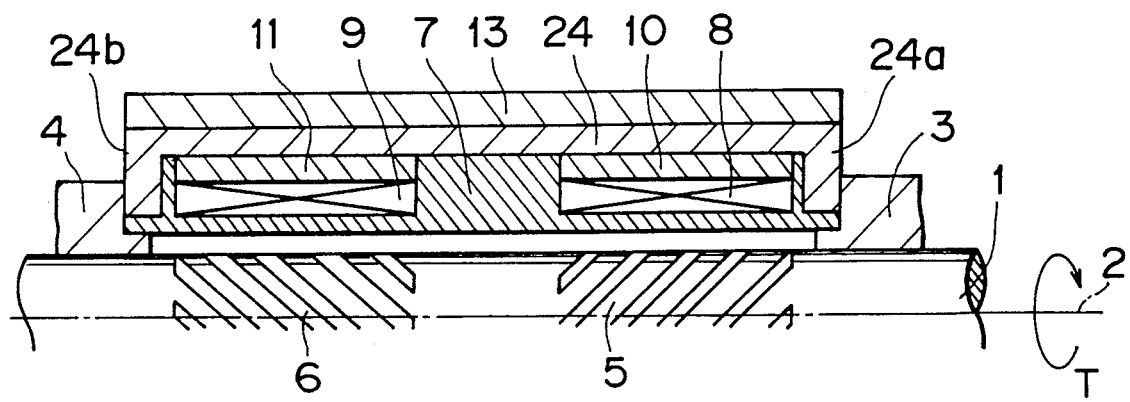
FIG. 3 is a partial schematic sectional view of a strain detector showing a third preferred embodiment of the present invention.
Figure 9:
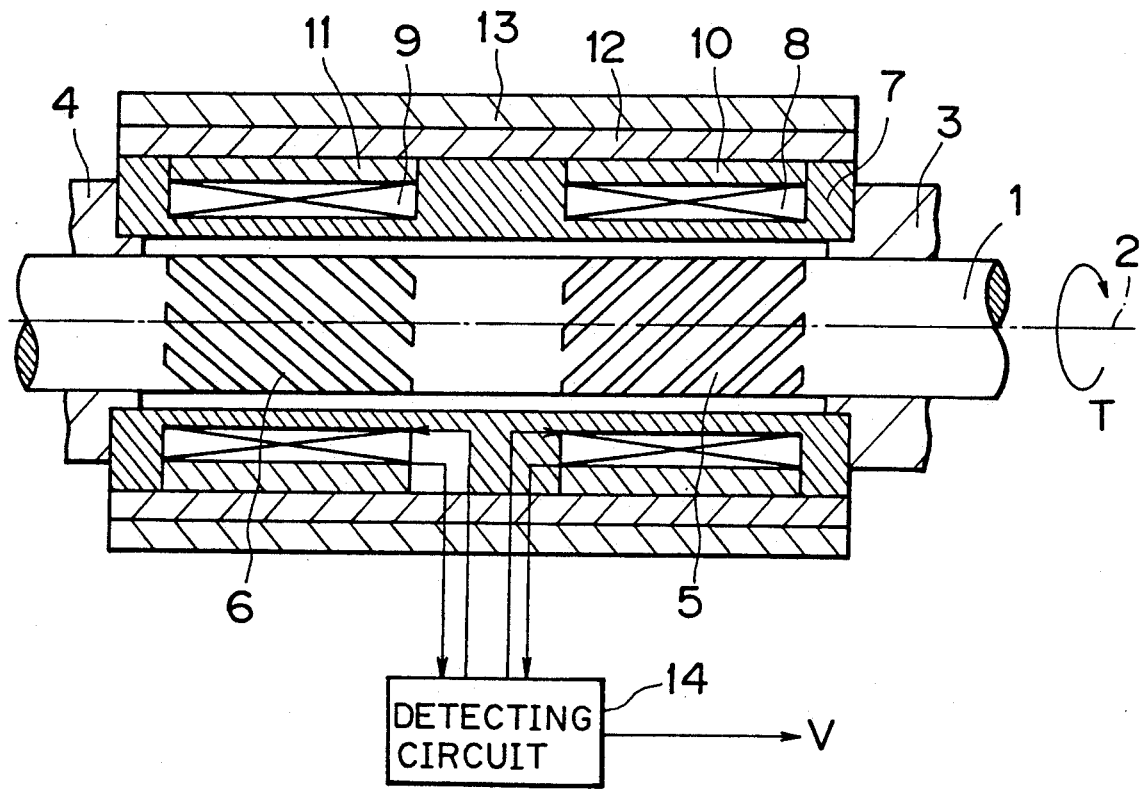
FIG. 9 is a schematic sectional view showing another conventional strain detector.

Referring now to FIG. 3, there is shown part of a strain detector of a third embodiment of the present invention. The detector of this embodiment has a generally similar construction to that of the conventional detector shown in FIG. 9 but is different in that it includes, in place of the shield 12 made of a non-magnetic material having a high electric conductivity such as copper or aluminum, a first shield 24 made of a non-magnetic material having a high electric conductivity such as copper or aluminum. The first shield 24 covers over outer peripheries of the yokes 10 and 11 and has a pair of flanges 24a and 24b projected radially inwardly from the opposite ends thereof so that it may have a channel-shaped section taken in a plane defined by the axial line 2 and a radial line of the shield 24 as seen in FIG. 3.

With this detector, since the first shield 24 is formed from a non-magnetic material having a high electric conductivity, the depth of penetration of an alternating magnetic field is reduced to a very small value due to a skin effect of the first shield 24. Consequently, internal magnetic fields produced by the detecting coils 8 and 9 and an external magnetic field are magnetically separated from each other by the first shield 24. Besides, since the shield 24 has a channel-shaped section, such magnetic separation is effected not only in a diametrical direction but also in an axial direction. Accordingly, invasion of an external alternating magnetic field into the detector is prevented with certainty, and the magnetic operating points of the magnetic layers 5 and 6 are not displaced and an error in detection does not take place. Further, since leakage of an internal magnetic field is prevented by the shield 24, the sensitivity of the detector is improved.

Figure 4:
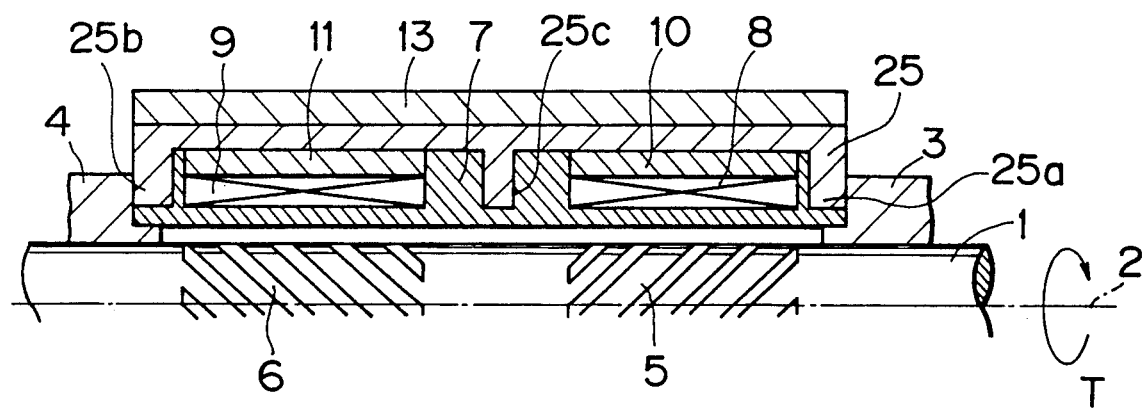
FIGS. 4 and 5 are similar views but showing fourth and fifth preferred embodiments of the present invention, respectively.

FIG. 4 shows a strain detector of a fourth embodiment of the present invention. This detector is similar in construction to the detector of the third embodiment shown in FIG. 3 but is only different in that it includes, in place of the first shield 24, a first shield 25 made of a non-magnetic material having a high electric conductivity and having three flanges 25a, 25b and 25c projected radially inwardly from the opposite ends and the axial center thereof so that it may have an E-shaped section taken in a plane defined by the axial line 2 and a radial line of the shield 25. The coil bobbin 7 has an annular groove formed in an outer wall at the axial center thereof for receiving the flange 25c of the first shield 25.

Also with the detector of this embodiment, magnetic separation takes place in a diametrical direction and also in an axial direction similarly as in the detector shown in FIG. 3. With this detector, however, further magnetic separation between the detecting coils 8 and 9 is effected by the flange 25c of the shield 25 extending into a spacing between the detecting coils 8 and 9, thereby preventing possible magnetic interference between the detecting coils 8 and 9. Accordingly, the sensitivity of the detector is improved and the distance between the detecting coils 8 and 9 can be decreased to permit miniaturization.

Figure 5:
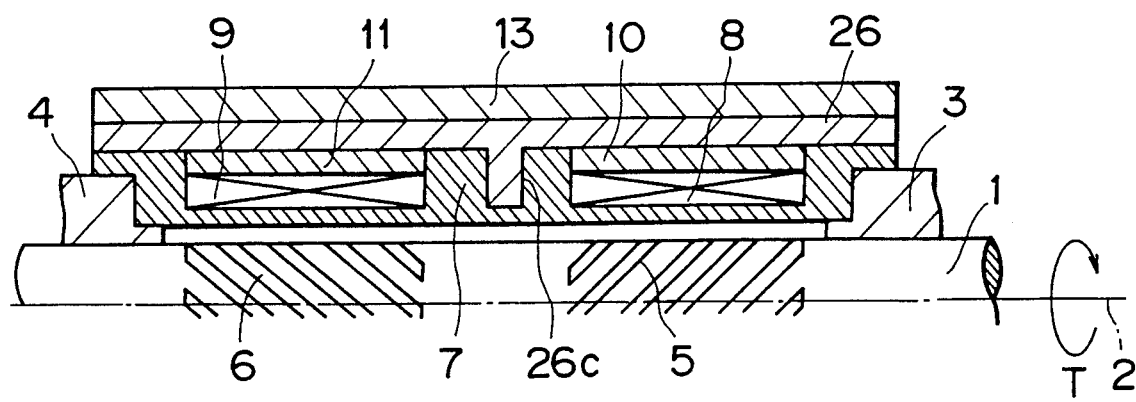

FIG. 5 shows a strain detector of a fifth preferred embodiment of the present invention. This detector is substantially similar to the detector shown in FIG. 4 but is different in that it includes, in place of the first shield 25, a first shield 26 made of a non-magnetic material having a high electric conductivity and only having a flange 26c projected radially inwardly from the axial center thereof so that it may have a T-shaped section taken in a plane defined by the axial line 2 and a radial line of the shield 26. Thus, the first shield 26 has no flanges that correspond to the flanges 25a and 25b of the first shield 25 of the detector of FIG. 4. Instead, the opposite axial end portions of the first shield 26 which extend over and around the yokes 10 and 11 are positioned around the bearings 3 and 4 with axial extensions of the coil bobbin 7 interposed therebetween so as to establish magnetic connection between the shield 26 and the bearings 3 and 4. With the detector of the present embodiment, magnetic separation between the detecting coils 8 and 9 is effected by the flange 26c of the first shield 26.

Figure 6:
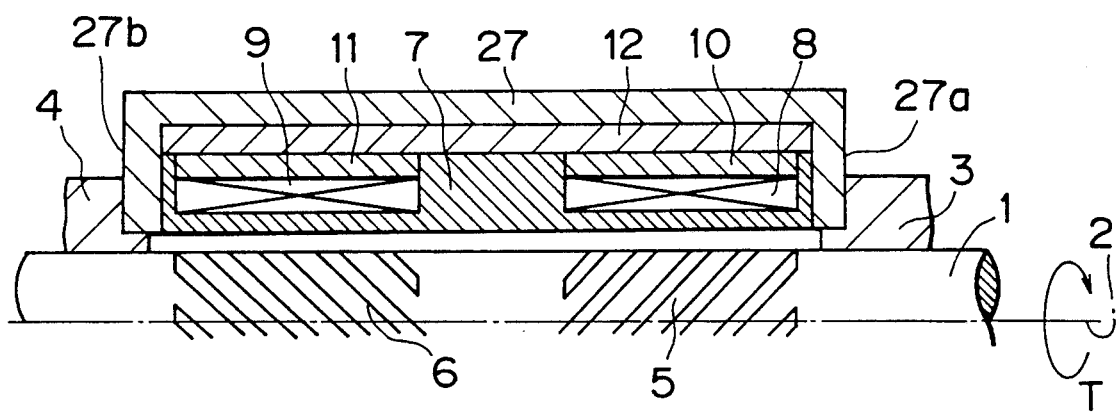
FIG. 6 is a similar view but showing a sixth preferred embodiment of the present invention.

Referring now to FIG. 6, there is shown a strain detector of a sixth preferred embodiment of the present invention. This detector has a substantially similar construction to that of the conventional detector shown in FIG. 9 but is different in that it includes, in place of the second magnetic shield 13, a magnetic shield 27 made of a soft magnetic material having a high permeability and having a pair of flanges 27a and 27b projected radially inwardly from the opposite ends thereof so that it may have a channel-shaped section taken in a plane defined by the axial line 2 and a radial line of the shield 27. The magnetic shield 27 is supported and magnetically connected at the opposite ends thereof on the bearings 3 and 4 and covers over outer peripheries of the yokes 10 and 11.

With the detector of the construction, since the magnetic shield 27 is formed with a channel-shaped section from a soft magnetic material having a high permeability, not only an external direct current magnetic field which tends to enter in a diametrical direction of the driven shaft 1 into the detector but also another external direct current magnetic field which tends to enter in an axial direction are interrupted by the magnetic shield 27. Consequently, the magnetic operating points of the magnetic layers 5 and 6 are not displaced, and an error in detection does not take place.

Figure 7A:
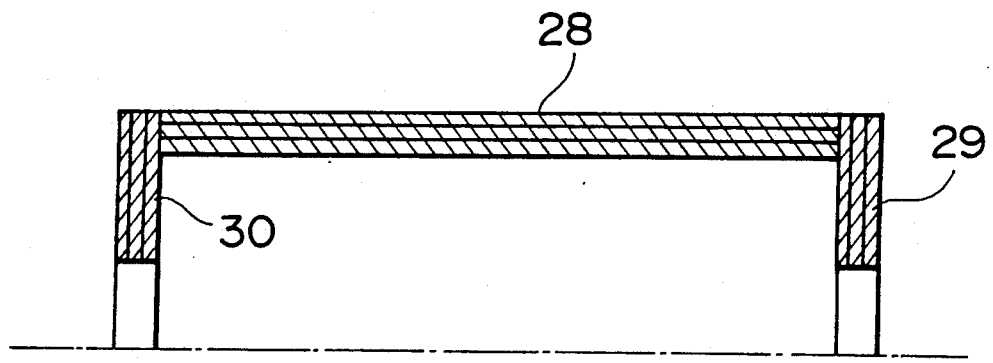
FIGS. 7a, 7b and 7c are sectional views showing different methods of forming a magnetic shield of the detector shown in FIG. 6.
Figure 7B:
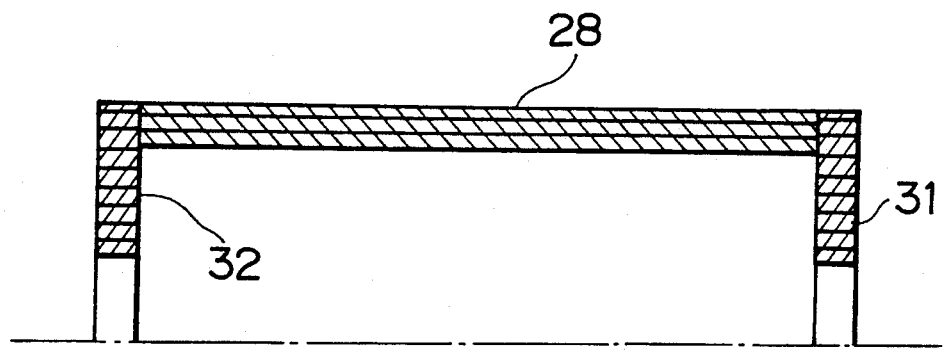
Figure 7C:
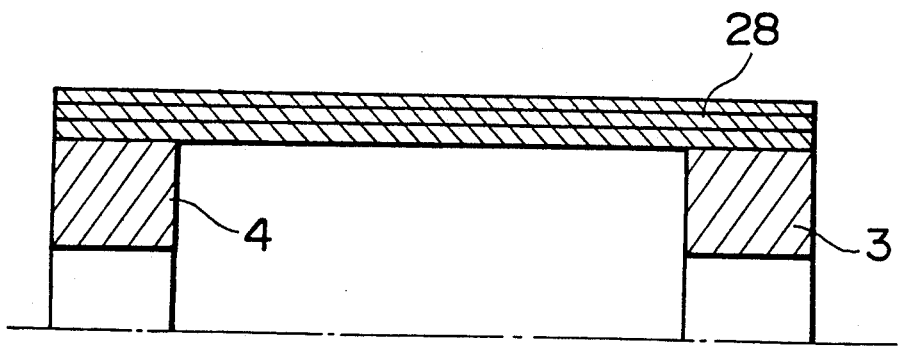
Figure 8:
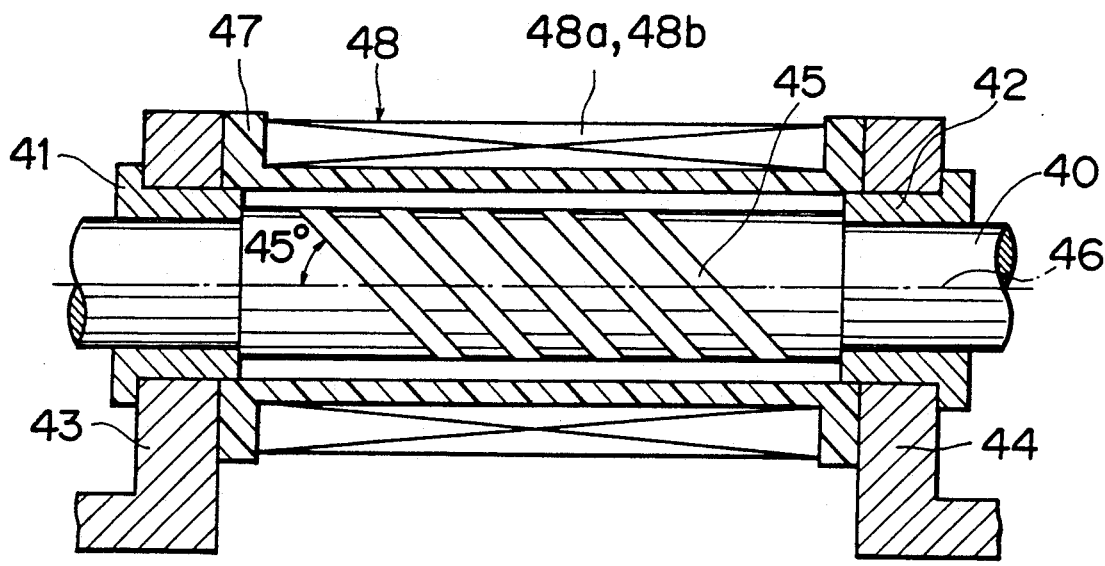
FIG. 8 is a schematic sectional view showing a conventional strain detector.

FIGS. 7a, 7b and 7c show different methods of forming the magnetic shield 27 as described above. In particular, referring first to FIG. 7a, a magnetic shield is formed by connecting a pair of doughnut-shaped portions 29 and 30 each formed from several flat plates layered one on another to the opposite ends of the cylindrical portion 28 formed from a soft magnetic plate having a high permeability and wrapped in several turns on itself. A magnetic shield shown in FIG. 7b is formed by connecting, to the opposite ends of a similar cylindrical portion 28, a pair of doughnut-shaped portions 31 and 32 each formed also from a soft magnetic plate having a high permeability and wrapped in several turns on itself. On the other hand, a magnetic shield shown in FIG. 7c is formed by connecting, to the opposite ends of a similar cylindrical portion 28, a pair of magnetic bearings 3 and 4 made of a soft magnetic material having a high permeability such that it may have a channel-shaped section taken in a plane defined by an axial line and a radial line of the shield.

Having now fully described the invention, it will be apparent to one of ordinary skill in the art that many changes and modifications can be made thereto without departing from the spirit and scope of the invention as set forth herein.

What is claimed is:

1. A strain detector for detecting strain in a driven shaft to which an external force is applied, comprising a magnetic layer made of a soft magnetic material having a high permeability and suitable magnetostriction fixedly mounted on an outer periphery of said driven shaft, a pair of bearings or bearing stands made of a soft magnetic material having a high permeability for supporting said driven shaft for rotation thereon, a detecting coil disposed around said magnetic layer for detecting a variation of the permeability of said magnetic layer arising from strain of said magnetic layer caused by an external force applied to said driven shaft, and a shield disposed on an outer periphery of said detecting coil and magnetically connected at the axial opposite end portions thereof to said bearings or bearing stands.

2. A detector as claimed in claim 1, wherein said shield is made of a soft magnetic material having a high permeability and has a pair of flanges extending radially inwardly from the opposite ends thereof in such a manner as to define a channel-shaped section taken in a plane defined by the axial line and a radial line of said shield.

3. A strain detector for detecting strain in a driven shaft to which an external force is applied, comprising a magnetic layer made of a soft magnetic material having a high permeability and suitable magnetostriction fixedly mounted on an outer periphery of said driven shaft, a pair of bearings or bearing stands made of a soft magnetic material having a high permeability for supporting said driven shaft for rotation thereon, a detecting coil disposed around said magnetic layer for detecting a variation of the permeability of said magnetic layer arising from strain of said magnetic layer caused by an external force applied to said driven shaft, and a shield disposed on an outer periphery of said detecting coil wherein said shield is made of a non-magnetic material having a high electric conductivity and has a pair of flanges extending radially inwardly from the opposite ends thereof in such a manner as to define a channel-shaped section taken in a plane defined by the axial line and a radial line of said shield.

4. A strain detector for detecting strain in a driven shaft to which an external force is applied, comprising a magnetic layer made of a soft magnetic material having a high permeability and suitable magnetostriction fixedly mounted on an outer periphery of said driven shaft, a pair of bearings or bearing stands made of a soft magnetic material having a high permeability for supporting said driven shaft for rotation thereon, a detecting coil disposed around said magnetic layer for detecting a variation of the permeability of said magnetic layer arising from strain of said magnetic layer caused by an external force applied to said driven shaft, and a shield disposed on an outer periphery of said detecting coil wherein said shield is made of a non-magnetic material having a high electric conductivity and has a flange projecting radially inwardly from an axial center thereof to define a T-shaped section taken in a plane including the axial line and a radial line of said shield.

* * * * *